(12) United States Patent
Orchard

(10) Patent No.: US 12,247,913 B2
(45) Date of Patent: Mar. 11, 2025

(54) SYSTEM AND METHODS FOR ANALYSIS OF A FLUID

(71) Applicant: S.C.R. (ENGINEERS) LIMITED, Netanya (IL)

(72) Inventor: Robert Graham Orchard, Hamilton (NZ)

(73) Assignee: S.C.R. (ENGINEERS) LIMITED, Netanya (IL)

( * ) Notice: Subject to any disclaimer, the term of this patent is extended or adjusted under 35 U.S.C. 154(b) by 213 days.

(21) Appl. No.: 17/905,417

(22) PCT Filed: Mar. 3, 2021

(86) PCT No.: PCT/NZ2021/050034
§ 371 (c)(1),
(2) Date: Sep. 1, 2022

(87) PCT Pub. No.: WO2021/177841
PCT Pub. Date: Sep. 10, 2021

(65) Prior Publication Data
US 2023/0129837 A1   Apr. 27, 2023

(30) Foreign Application Priority Data

Mar. 3, 2020   (NZ) ........................................ 762276

(51) Int. Cl.
*G01N 21/25* (2006.01)
*A01J 5/007* (2006.01)
*G01N 33/04* (2006.01)

(52) U.S. Cl.
CPC .............. *G01N 21/25* (2013.01); *A01J 5/007* (2013.01); *G01N 33/04* (2013.01)

(58) Field of Classification Search
CPC . A01J 5/007; G01N 21/25; G01N 2291/0228; G01N 2291/02466;
(Continued)

(56) References Cited

U.S. PATENT DOCUMENTS

2007/0272159 A1* 11/2007 Francke ................ A01J 5/0137
119/14.14

FOREIGN PATENT DOCUMENTS

| CA | 2820857 A1 | 6/2012 |
| GB | 2472503 A | 2/2011 |
| WO | 2019093907 A1 | 5/2019 |

OTHER PUBLICATIONS

Agreement between milk fat, protein, and lactose observations collected from the Dairy Herd Improvement Association (DHIA) and a real-time milk analyzer | K. Kaniyamattam, A. De Vries | Open Archive Published: Mar. 17, 2014 | DOI:https://doi.org/10.3168/jds.2013-7690 | vol. 97, Issue 5, p. 2896-2908, May 1, 2014.

* cited by examiner

*Primary Examiner* — Tri T Ton
(74) *Attorney, Agent, or Firm* — Keith O'Doherty

(57) ABSTRACT

Systems and methods for analysing milk are described. A plurality of First Type Sensors (FTPs) are provided, each associated with a respective one of a plurality of Milking Clusters (MKs) of a milking system and configured to analyse milk extracted from an animal by the MK to determine at least one FTP value of a parameter of the milk across an event period. At least one of a Second Type Sensor (STP) associated with at least one of the plurality of MKs is configured to analyse the milk to determine at least one STP value of the parameter within the event period, wherein the STP is less susceptible to animal specific bias than the FTP. An Animal Specific Bias Correction (ASBC) is determined based on the at least one FTP value and the at least one STP value and applied to FTP values for milk extracted from the animal.

17 Claims, 8 Drawing Sheets

(58) Field of Classification Search
CPC ....... G01N 29/02; G01N 33/04; B25J 13/085; B25J 19/02; B25J 9/161; B25J 9/163; B25J 9/1653; G05B 23/02
USPC .... 356/402, 243.2, 246, 134, 409, 410, 415, 356/441, 249
See application file for complete search history.

SYSTEM AND METHODS FOR ANALYSIS OF A FLUID

STATEMENT OF CORRESPONDING APPLICATIONS

This application is based on the specification filed in relation to New Zealand Patent Application Number 762276, the entire contents of which are incorporated herein by reference.

TECHNICAL FIELD

The present disclosure relates to systems and methods for analysis of a fluid, more particularly for analysis of milk using sensing devices within a milking environment.

BACKGROUND

The use of sensors to obtain information relating to milk collected from dairy animals is well known. Such information is used in decision making regarding such matters as processing of the milk, culling, breeding, medical treatment, animal specific feed rations as well as measurement of milk production efficiency.

In some milking systems, in-line sensors are provided that are capable of collecting data across the entirety of a milking, sensing characteristics of the milk flowing through them. Ideally, such sensors are installed for each bail of a milking system in order to allow for collection of data from individual animals at a high frequency (in terms of data being collected each time the animal is milked).

However, in order to achieve an acceptable price-point to allow for installation in quantities to provide a high bail coverage, and to meet the constraints imposed by flowing milk, such in-line sensors are generally of lower precision than other known sensor types. This impacts the quality or certainty of the data collected, and therefore the effectiveness of decision making based on that data.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Further aspects and advantages of the present invention will become apparent from the ensuing description which is given by way of example only.

SUMMARY

According to one aspect of the present technology there is provided a system for analysing milk, including:
a plurality of first type sensors, each first type sensor associated with a respective one of a plurality of milking clusters of a milking system and configured to analyse milk extracted from an individual animal by the milking cluster to determine at least one first type sensor value of a parameter of the milk across an event period;
at least one of a second type sensor associated with at least one of the plurality of milking clusters and configured to analyse the milk extracted from the individual animal by the milking cluster to determine at least one second type sensor value of the parameter of the milk within the event period, wherein the second type sensor is less susceptible to animal specific bias than the first type sensor, and wherein the number of the second type sensor in the system is less than the number of first type sensors; and
at least one processor configured to:
determine an animal specific bias correction for the individual animal based on the at least one first type sensor value of the parameter and the at least one second type sensor value of the parameter determined for the individual animal; and
applying the animal specific bias correction to first type sensor values of the parameter obtained from the first type sensors for milk extracted from the individual animal.

According to one aspect of the present disclosure there is provided a method for analysing milk in a system having a plurality of milking clusters, each configured to extract milk from an individual animal, the method including:
analysing milk extracted from an individual animal by a milking cluster, using a first type sensor associated with the milking cluster, to determine at least one first type sensor value of a parameter of the milk across an event period;
analysing the milk extracted from the individual animal by the milking cluster, using a second type sensor associated with the milking cluster, to determine at least one second type sensor value of the parameter of the milk within the event period, wherein the second type sensor is less susceptible to animal specific bias than the first type sensor, and wherein the number of the second type sensor in the system is less than the number of first type sensors; and
determining an animal specific bias correction for the individual animal based on the at least one first type sensor value of the parameter and the at least one second type sensor value of the parameter determined for the individual animal; and
applying the animal specific bias correction to the first type sensor values of the parameter obtained from the first type sensors for milk extracted from the individual animal.

Numerous sensors exist for the automated sensing of a variety of parameters of milk, including various components of milk (for example, but not limited to, one or more of fat, protein, and lactose), as well as attributes such as the volume of milk extracted—i.e. yield. Animal specific bias of sensor measurements can occur when one or more attributes of milk, or the animal itself, that influence a measurement of the target parameter vary between animals but remain relatively consistent for an individual animal. For example, if measurement of milk fat is influenced by milk colour, then the concentration of molecular compounds that affect milk colour will likely affect the measurement. If animals within a group have different, but persistent, concentrations of these compounds, they will each bias the measurement in accordance with their respective concentrations, resulting in animal specific bias. It is believed that animal specific bias may be more apparent in more genetically diverse groups of animals, for example multi-breed groups of animals, with the genetic diversity contributing to greater variation in the aforementioned milk attributes. Sensors exhibiting animal specific bias produce measurement results for individual animals which tend to be biased relative to other animals in a group of animals, therefore impacting between animal comparisons and decisions based on those comparisons.

As such, reference to a correction for animal specific bias should be understood to mean a correction (for example, a value or a function) associated with an individual animal to be applied to measurements of parameter(s) of milk extracted from that animal, where the animal specific bias is determined for a particular type of sensor. It should be noted that means for identifying an individual animal, and recording data collected for milk extracted from that animal, are well known in the art.

In examples, the first type sensors may be optical sensors. Numerous such sensors are known for use in relation to milking animals. By way of example, the first type sensor may be the Protrack™ volume, fat, and protein sensor by LIC Automation Limited (www.licautomation.co.nz), the AfiLab™ fat, protein and lactose concentration sensor by Afimilk Ltd (www.afimilk.com), or the Lely MQC™ fat and protein concentration sensor by Lely (www.lely.com).

Optical sensors can be sensitive to optical properties of milk, particularly milk colour and/or to the degree of optical scattering. As such, it is believed that optical sensors may exhibit animal specific bias related to milk attributes that contribute to milk colour and optical scattering. It should be appreciated that while reference may be made to the first type sensors being optical based sensors, it is expressly contemplated that examples of the present technology may be applied to systems using other sensor types which are susceptible to animal specific bias.

In examples, it is envisaged that the first type sensors may be in-line sensors. Reference herein to an in-line sensor should be understood to mean a sensor analysing fluid flowing past one or more sensing means, to determine at least one parameter of the fluid at a particular point in time or across a period of time—i.e. without collection of a discrete sample from the flow. Milking plants typically include individual milk transport conduits from the points of extraction (for example, using a milking cluster including teat cups), joining to a common transport line for delivery to the storage vessel. The provision of in-line sensors within the individual milk transport conduits is known in the art—allowing for the analysis of milk extracted from an individual animal as it flows through those individual milk transport conduits. It is generally desirable to associate sensors with as high a percentage of the milking clusters as possible in order to achieve a high frequency of data collection for individual animals (i.e. data is collected each time they are milked).

As a further example, it is believed that animal specific bias may be observed in in-line volume measurements where the milk volume is derived from a cross sectional area of milk flow. It believed that between-animal variations in the shape or hair coverage of an animal's teats may result in differences in the amount of air entering the teat cups of the milking cluster. This may influence the cross-sectional area, velocity or air content of milk passing such an in-line sensor, potentially leading to a biased measurement.

The desire to install such sensors in relatively high numbers provides a practical driver to reduce their price-point, which contributes to their having a lower precision than other known sensors. Additionally, the fact that in-line milk sensors analyse the milk as it flows past them prevents the use of sample treatments that can improve measurement, as known in devices which analyse discrete samples of milk. For example, known ultrasound milk analysers control milk temperature precisely to achieve higher precision measurement. Known mid-infrared analysers also control milk temperature and require a measurement cell much narrower than typical conduits for milk flow in which in-line sensors are positioned. Other treatments—including elimination of air bubbles, addition of reagents, and homogenisation—can be used in sensors analysing discrete samples but not in-line sensors, and may improve measurement performance. Furthermore, in-line sensors need to be fabricated using materials and geometries in order to meet hygiene requirements for milking systems, which also contributes to their relatively low precision. For completeness, it is envisaged that aspects of the present technology may be applied to systems utilising first type sensors which are not configured to be installed in-line.

Conversely, it is not generally commercially viable to install sensors which are less susceptible to animal specific bias and generally higher precision (i.e. the second type sensor) for each milking cluster due to cost considerations (for example due to high capital costs, or ongoing use of consumables). For example, the second type sensor may utilise measurement techniques using ultrasound, acoustics, electromagnetic radiation (for example, near-infrared, or mid-infrared), and electronic impedance. By way of example, the second type sensor may implement the sensing methodology performed by the off-line LactiCheck™ milk analyser by Page & Pedersen International, Ltd (www.page-pedersen.com) or the off-line MIRIS™ Dairy Milk Analyzer by Miris Holding AB (www.mirissolutions.com). An example of a second sensor type for volume may be a 'fill and dump' type milk meter, examples of which include the AfiMilk™ MPC Milk Meter by Afimilk Ltd (www.afimilk.com) and Metatron™ Milk Meter by GEA Group AG (www.gea.com). At present, some known examples of the second type sensor require the extraction of a sample of the milk for analysis. However, it is contemplated that an in-line second type sensor may become available in the future—but the present technology will remain applicable where such sensors are relatively costly compared to the first type sensor type.

In examples, the second type sensor may be a sensor system including multiple types of sensing device—for example, that of a first type sensor in addition to another sensor type—which collectively provide a measurement value which is less susceptible to animal specific bias than the first type sensor in isolation. Further details of such a sensor system may be found, for example, in PCT Patent Application No. PCT/NZ2018/050153, entitled "System and Method for Analysis of a Fluid", which is incorporated herein by reference. It should appreciated that in such examples, the animal specific bias correction may be determined based on sensor values from (a) the included first type sensor in isolation (i.e. "the at least one first type sensor value of the parameter"), and (b) the sensor system, which may be determined in part using the first type sensor value (i.e. "the at least one second type sensor value of the parameter"). Further, in such examples it should be appreciated that the animal specific bias correction may be applied to the values obtained from first type sensors other than those included in the second type sensor.

Aspects of the present technology compensate for the respective limitations of the first type sensors and the second type sensors by utilising the measurements of the second type of sensor to correct the measurements of the first type sensor to account for animal specific bias.

In examples, determining an animal specific bias value includes determining a difference between a first type sensor value of the parameter and a second type sensor value of the parameter each time the animal is milked using a milking cluster having an associated first type sensor and second type sensor.

In examples, determining the animal specific bias value includes determining an average of the difference between a first type sensor value of the parameter and a second type sensor value of the parameter over a time period including a plurality of instances of the animal being milked.

In an example the time period may be a full lactation (i.e. for a dairy cow, the period of time between one calving and the next during which the cow produces milk). In an example the time period may be part of a lactation—e.g. one or more stages of the lactation cycle.

In examples the animal specific bias correction may be applied retrospectively, i.e. at the end of the time period the animal specific bias correction may be applied to past low precision results. It is envisaged that this may be particularly applicable where the results are to be used for purposes such as animal evaluation at the end of a season.

In examples a moving animal specific bias correction may be used from the start of the time period, for example to be applied for day-to-day animal management purposes. It is anticipated that multiple results may be required before the animal specific bias correction becomes reliable. It should be appreciated that results could continue to be updated retrospectively as new data was obtained, i.e. overwrite corrected results once a new data point for the animal was obtained and the animal specific bias correction updated.

In an example, determining the animal specific bias correction accounts for trends across a time period. For example, the animal specific bias value may be determined by fitting a curve to a relationship of the difference between the first type sensor value of the parameter and the second type sensor value of the parameter over time. For example, it is envisaged that animal specific bias may drift throughout a lactation. To account for this, an equation may be fitted for each animal that calculates the animal specific bias correction from a predetermined time (for example, days since calving).

In examples, determination of the animal specific bias correction may exclude data from an instance of an animal being milked where a first type sensor value of the parameter and/or a second type sensor value of the instance are determined to be outliers within the time period. In examples, once the animal specific bias correction has been determined, a first type sensor value of the parameter may be adjusted by the animal specific bias correction to provide a correction of error—i.e. produce a corrected first type sensor value of the parameter. For completeness, it should be appreciated that reference to correction of error is intended to mean a reduction in at least the animal specific component of error in comparison with measurements determined from the first type sensor alone.

In examples, determination of whether a value of the parameter is an outlier may include determination of whether the value of the parameter is an implausible result—i.e. not being within a plausible biological range. In examples, determination of whether a value of the parameter is an outlier may include determination of whether the value of the parameter is a 'contemporary group' outlier—i.e. a statistical outlier compared with results for other animals within the contemporary group. A contemporary group is defined as a group of animals having one or more comparable demographics (e.g. breed, age, and/or stage of lactation). In examples, determination of whether a value of the parameter is an outlier may include determination of whether the value of the parameter is a within-animal outlier—i.e. a statistical outlier compared with other results for the same animal at a similar stage of lactation. In examples, determination of whether a value of the parameter is an outlier may include determination of whether the value of the parameter is a within-animal difference outlier—i.e. a result from a milking where the difference between first type sensor results and second type sensor results is a statistical outlier compared with the differences for other milkings from the same animal at a similar stage of lactation.

In examples, the values for the parameter in respective datasets including the first type sensor values and the second type sensor values may be calibrated for general bias. In examples the median value of the second type sensor results across all bails for a particular day may be determined to provide a reference for calibration. In examples the median of the first type sensor value of the parameter for each bail for the day may be determined. In examples, an adjustment value for the day may be determined as the difference between the median value of the second type sensor results across all bails and the median of the first type sensor value of the parameter for each bail.

For a firmware and/or software (also known as a computer program) implementation, the techniques of the present disclosure may be implemented as instructions (for example, procedures, functions, and so on) that perform the functions described. It should be appreciated that the present disclosure is not described with reference to any particular programming languages, and that a variety of programming languages could be used to implement the present invention. The firmware and/or software codes may be stored in a memory, or embodied in any other processor readable medium, and executed by a processor or processors. The memory may be implemented within the processor or external to the processor. A processor may be a microprocessor, but in the alternative, the processor may be any processor, controller, microcontroller, state machine, or cloud computing device known in the art. A processor may also be implemented as a combination of computing devices, for example, a combination of a digital signal processor (DSP) and a microprocessor, a plurality of microprocessors, one or more microprocessors in conjunction with a DSP core, or any other such configuration. The processors may function in conjunction with servers and network connections as known in the art. By way of example, the first type sensors and second type sensors and a central processor may communicate with each other over a Controller Area Network (CAN) bus system. In the context of milking, other performance sensors (for example flow or yield sensors), animal identification devices, and milking plant sensors may also communicate with the central processor. In an exemplary embodiment, animal identifiers, data from the sensors, and any other data may be stored in a data cloud.

The steps of a method, process, or algorithm described in connection with the present disclosure may be embodied directly in hardware, in a software module executed by one or more processors, or in a combination of the two. The various steps or acts in a method or process may be performed in the order shown, or may be performed in another order. Additionally, one or more process or method steps may be omitted, or one or more process or method steps may be added to the methods and processes. An additional step, block, or action may be added in the beginning, end, or intervening existing elements of the methods and processes.

BRIEF DESCRIPTION OF DRAWINGS

Further aspects of the present technology will become apparent from the following description which is given by way of example only and with reference to the accompanying drawings in which.

DETAILED DESCRIPTION

Aspects of the present technology are described herein in the context of analysis of milk. However, it should be appreciated that principles of the disclosure discussed herein may be applied to the analysis of other fluids.

Figure 1A:
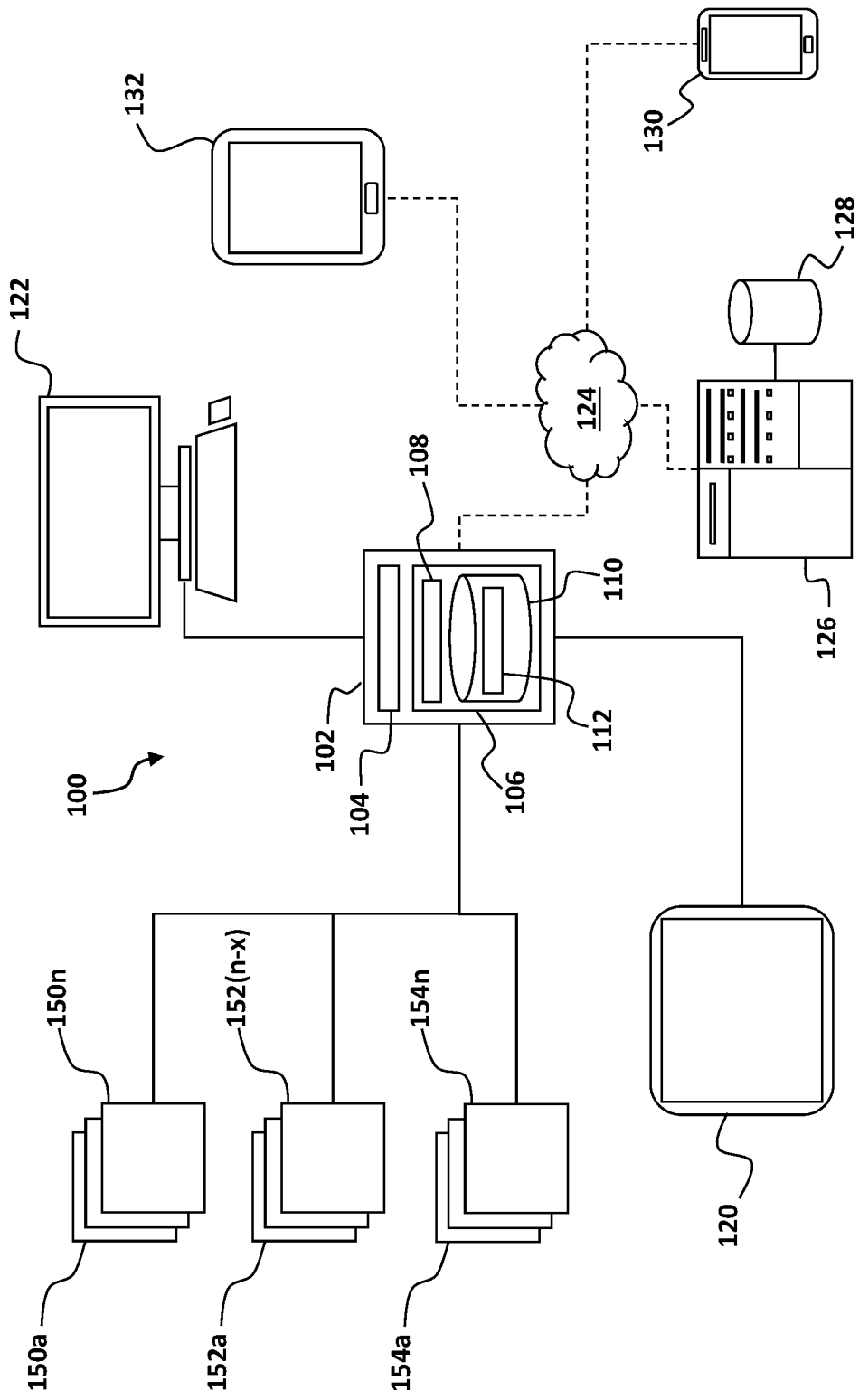
FIG. 1A is a schematic diagram of an exemplary livestock management system in which an aspect of the present technology may be implemented.

FIG. 1A illustrates a livestock management system 100, within which a local hardware platform 102 manages the collection and transmission of data relating to operation of a milking facility. The hardware platform 102 has a processor 104, memory 106, and other components typically present in such computing devices. In the exemplary embodiment illustrated the memory 106 stores information accessible by processor 104, the information including instructions 108 that may be executed by the processor 104 and data 110 that may be retrieved, manipulated or stored by the processor 104. The memory 106 may be of any suitable means known in the art, capable of storing information in a manner accessible by the processor 104, including a computer-readable medium, or other medium that stores data that may be read with the aid of an electronic device. The processor 104 may be any suitable device known to a person skilled in the art. Although the processor 104 and memory 106 are illustrated as being within a single unit, it should be appreciated that this is not intended to be limiting, and that the functionality of each as herein described may be performed by multiple processors and memories, that may or may not be remote from each other. The instructions 108 may include any set of instructions suitable for execution by the processor 104. For example, the instructions 108 may be stored as computer code on the computer-readable medium. The instructions may be stored in any suitable computer language or format. Data 110 may be retrieved, stored or modified by processor 104 in accordance with the instructions 110. The data 110 may also be formatted in any suitable computer readable format. Again, while the data is illustrated as being contained at a single location, it should be appreciated that this is not intended to be limiting—the data may be stored in multiple memories or locations. The data 110 may also include a record 112 of control routines for aspects of the system 100.

The hardware platform 102 may communicate with various devices associated with the milking facility, for example: a first type of sensor 150a to 150n associated with a plurality of individual milking clusters within the milking facility, and a second type of sensor 152a to 152(n-x) associated with a subset of the individual milking clusters. Reference may be made herein to milk being collected at or from a bail. A bail is a locale within a milking facility at which an animal may be positioned for milking. In some milking facilities, milking clusters are associated with a bail in a one to one relationship (for example, in a typical rotary milking parlour), while in others a milking cluster may be shared between two or more bails (for example, in a herringbone configuration).

Figure 1B:
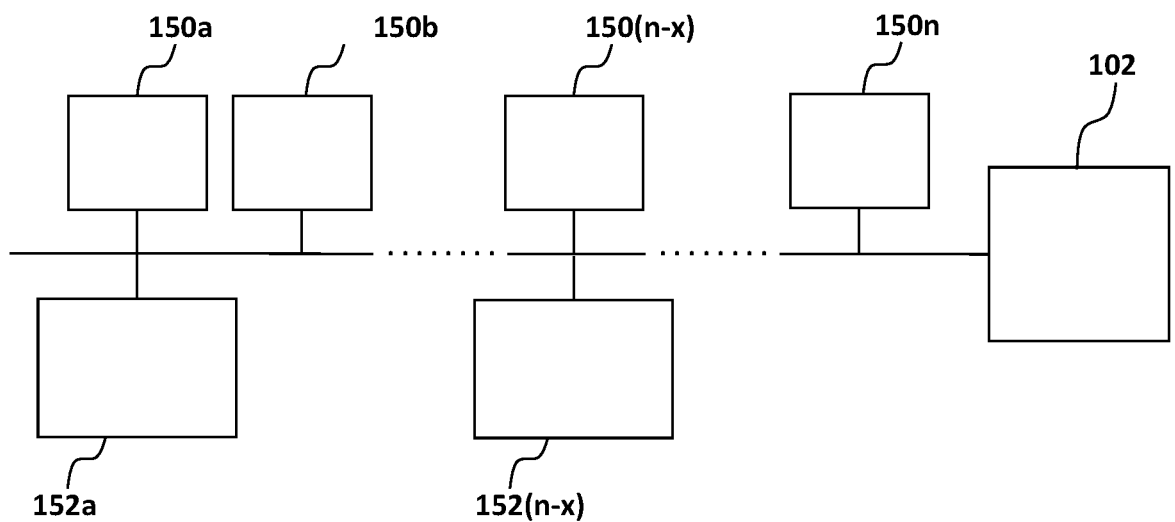
FIG. 1B is a schematic diagram of a first exemplary sensor arrangement for use in the exemplary livestock management system.

FIG. 1B illustrates the first type sensors 150a to 150n and second type sensors 152a to 152(n-x) connected over a Controller Area Network (CAN) bus with the hardware platform 102. It should be appreciated that while not illustrated, additional performance sensors (for example performance sensors such as milk flow or yield sensors) may also be connected to, and communicate over, the CAN bus. Each of the first type sensors 150a to 150n and second type sensors 152a to 152(n-x) are associated with an individual milking cluster in the milking facility—i.e. the sensor data output by an individual sensor relates to milk from an individual animal being milked by that milking cluster.

In examples the first type sensor 150 may be an in-line sensor configured to determine at least the fat and/or protein content of milk—for example the Protrack Milk™ volume, fat, and protein sensor by LIC Automation Limited, or the AfiLab™ fat, protein and lactose concentration sensor by Afimilk Ltd, or the Lely MQC™ fat and protein concentration sensor by Lely. In exemplary embodiments, a first type sensor 150 may be provided for each milking cluster in the milking facility. However, it should be appreciated that this is not intended to be limiting to every embodiment of the present disclosure. For example, it is contemplated that only a subset of milking clusters may have associated first type sensors 150.

In accordance with aspects of the present technology, second type sensors 152a to 152(n-x) are provided on a less than one to one basis with the first type sensors 150a to 150n—i.e. second type sensors 152a to 152(n-x) are only provided for a sub-set of those milking clusters also having first type sensors 150a to 150n.

The second type sensor 152 is configured to analyse milk for at least one of the same parameter(s) as the first type sensor 150—but less affected by animal specific bias. In examples the second type sensor 152 may implement an ultrasound-based sensing methodology as performed by the off-line LactiCheck™ milk analyser by Page & Pedersen International Ltd, or a mid-infrared based sensing methodology as performed by the off-line MIRIS™ Dairy Milk Analyzer by Miris Holding AB. In examples the second type sensor 152 is configured to analyse a sample of milk obtained from the milk extracted by the associated milking cluster (for example using a sampling device to deliver an extracted sample of milk to one of the aforementioned off-line sensors).

Figure 1C:
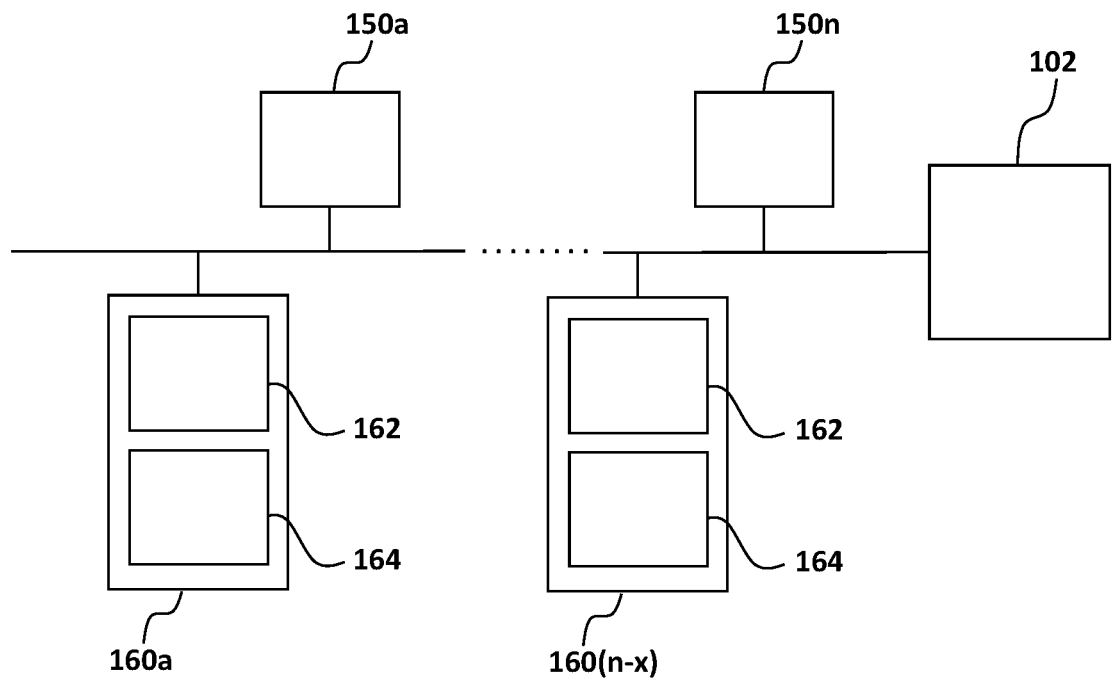
FIG. 1C is a schematic diagram of a second exemplary sensor arrangement for use in the exemplary livestock management system.

Referring to FIG. 1C, in an alternative example the second type sensor 152 may be a sensor system 160 including multiple types of sensing device—for example, a first system sensor 162 equivalent to the first type sensor 150, and a second system sensor 164. The results from the first system sensor 162 and the second system sensor 164 may be used collectively to produce a measurement value which is less susceptible to animal specific bias than a first type sensor 150 in isolation (i.e. providing a "second sensor type" value). Further details of operation of such a sensor system may be found, for example, in PCT Patent Application No. PCT/NZ2018/050153. It will be appreciated that the exemplary system sensor 160 may therefore produce both a first type sensor value and a second type sensor value for the analysed milk.

Returning to FIG. 1A, animal identification devices 154a to 154n are provided for determining an animal identification ("animal ID") of individual animals entering, or within, the milking facility. More particularly, the animal identification devices 154a to 154n may be used to associate an animal ID with each of the milking clusters associated with the first type sensors 150a to 150n (and second type sensors 152a to 152n), such that the sensor data may be attributed to the individual animals. A variety of methodologies are known for the determination of an animal ID—for example a radio frequency identification ("RFID") reader configured to read an RFID tag carried by the animal. In an alternative embodiment, or in conjunction with the animal identification devices 154a to 154n, a user may manually enter (or correct) animal IDs via a user device.

The hardware platform 102 may also communicate with user devices, such as touchscreen 120 located within the milking facility for monitoring operation of the system, and a local workstation 122. The hardware platform 102 may also communicate over a network 124 with one or more server devices 126 having associated memory 128 for the storage and processing of data collected by the local hardware platform 102. It should be appreciated that the server 126 and memory 128 may take any suitable form known in the art—for example a "cloud-based" distributed server architecture. The network 124 potentially comprises various configurations and protocols including the Internet, intranets, virtual private networks, wide area networks, local networks, private networks using communication protocols proprietary to one or more companies—whether wired or wireless, or a combination thereof. It should be appreciated that the network 124 illustrated may include distinct networks and/or connections: for example a local network over which the user interface may be accessed within the vicinity of the milking facility, and an internet connection via which the cloud server is accessed. Information regarding operation of the system 100 may be communicated to user devices such as a smart phone 130 or a tablet computer 132 over the network 124.

Figure 2:
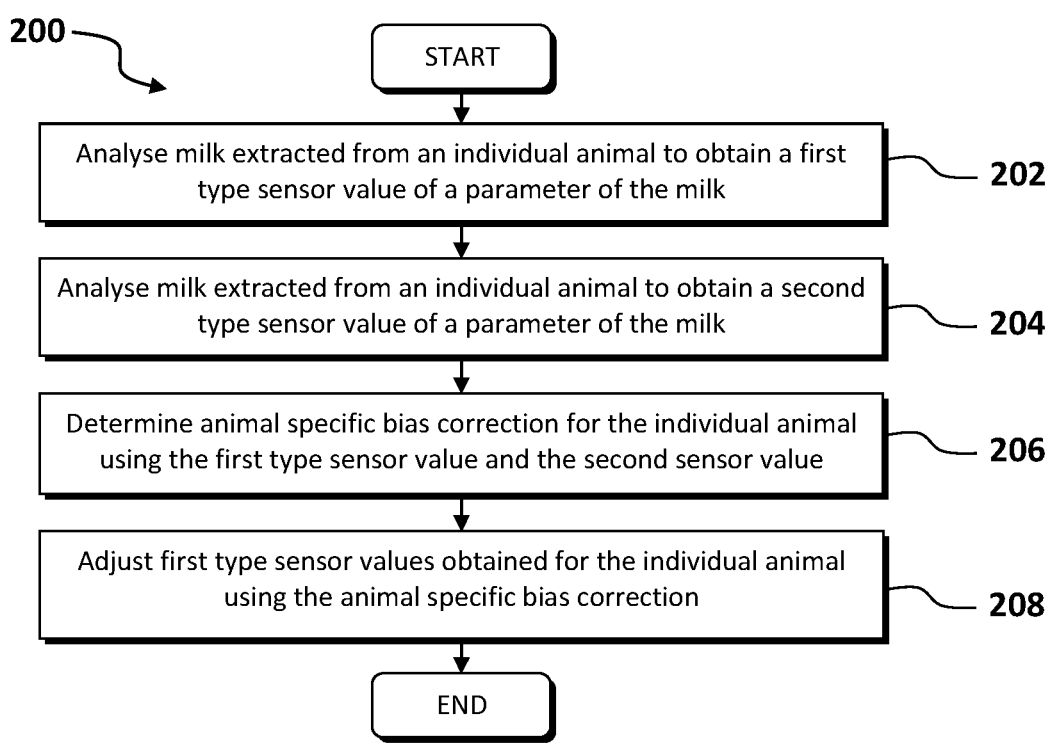
FIG. 2 is a flowchart of a method of analysing milk according to aspects of the present technology.

With reference to FIG. 2, a method 200 for analysing milk extracted from individual animals by system 100 is provided. In a first step 202, milk extracted from an individual animal by a milking cluster is analysed using an associated first type sensor 150 to obtain a first type sensor value of a parameter of the milk (for example, fat and/or protein content). The animal is identified and the animal identification recorded together with the first type sensor value. In a second step 204, the milk is also analysed by a second type sensor 152 associated with the same milking cluster to obtain a second type sensor value of the parameter of the milk, which is recorded against the animal identification.

In a third step 206, the first type sensor value and the second type sensor value of the parameter are used to determine an animal specific bias value for the individual animal. In an example, the animal specific bias value may be the difference between the first type sensor value and the second type sensor value for the parameter. In an example, the animal specific bias value is an average of the difference between the first type sensor value and second type sensor value over a time period including a plurality of instances of the animal being milked—for example, a lactation cycle or partial lactation cycle of the animal. In examples, the animal specific bias value may include regression coefficients determined by applying a linear regression to the difference between the first type sensor value and the second type sensor value for the animal's days-in-milk.

In examples, one or more automated outlier detection processes may be applied to datasets including the first type sensor values and the second type sensor values respectively, prior to determination of the animal specific bias value in order to remove such outliers. For example, an outlier detection process may be implemented in the form of a software script. In examples, outlier detection may include one or more of: determination of whether the value of the parameter is an implausible result, determination of whether the value of the parameter is a contemporary group outlier, determination of whether the value of the parameter is a within-animal outlier, and determination of whether the value of the parameter is a within-animal difference outlier.

In examples, the values for the parameter in the respective datasets including the first type sensor values and the second type sensor values may be calibrated for general bias. In examples, the second type sensor values may be calibrated for general bias using vat data as a reference, where vat data refers to values for the parameter obtained for milk collected from a vat in which milk from all bails is collected. In one embodiment, calibration for general bias may include determining (for each date that data is collected) the median value of the second type sensor results across all bails (the "all-bails second type median") to provide a reference for calibration. For each bail, the median of the first type sensor value of the parameter is determined (the "current-bail first type median"), and a bail-day adjustment is determined as the all-bails second type median minus the current-bail first type median. For all first type sensor results, the relevant bail-day adjustment may be applied by adding it to the original result to produce adjusted results for use in further processing. It is envisaged that this may reduce inter-bail bias, and consequently result in less noise in the individual estimates of animal specific bias. In examples, adjusted results may be excluded from further analysis if a predetermined number of results for that bail were not recorded for a particular day.

In a fourth step 208, the first type sensor values of the milk parameter are adjusted by subtracting the animal specific bias value from the first type sensor values obtained for the individual animal. These adjusted values may then be used in further data analysis and decision making as known in the art.

It is envisaged that aspects of the present technology may have particular application to examples in which the system 100 is installed in a rotary milking parlour. Some milking animals, for example cows, can be highly consistent in the order they present themselves for milking. As a result, in some milking parlour configurations there may be a relatively high potential for an animal to be consistently milked at the same or similar bail milking cluster. This may result in a situation where certain animals are less likely to be milked by a milking cluster having an associated second type sensor which may be used to determine animal specific bias for that animal. In a rotary milking parlour, the order in which animals present themselves for milking does not have an effect on allocation to a particular bail, as the milking platform is continuously rotating. As a result, the allocation of an animal to a bail with an associated second type sensor is essentially random—thereby increasing the likelihood of an animal specific bias correction being developed for each animal within the group.

In examples, the order of animals entering a milking parlour may be controlled (for example, using drafting gates) to encourage distribution of animals to bails having second type sensors.

Experimental example: correcting fat and protein sensor results obtained using Protrack™ Milk The following describes an experimental implementation of the present technology in the form of the correction of fat and protein sensor results obtained using Protrack™ Milk ("PT-Milk") sensors. PT-Milk sensors were installed on 17 bails, with second type sensors (in the form of sensor systems 160 as described above with reference to FIG. 1C, where the first system sensor 162 used the same sensing methodology as PT-Milk and the second system sensor 164 was an ultrasound-based sensor) installed on 17 other bails—i.e. sensors were installed on 34 bails in total.

In this example, the sensor results for fat and protein were adjusted by comparing the seven day mean to the average results from regularly acquired milk samples tested using a laboratory-based reference method (referred to herein as "herd test"). It is noted that in practice the sensors may be regularly calibrated by comparison to the herd average fat and protein determined by bulk milk sample results provided by a milk processing company, and that this form of result adjustment may therefore not be required. In alternative examples, the general bias correction described above may be utilised.

In this experimental implementation, data from 31 cows was used to calculate performance metrics, being animals having at least eight milkings with valid herd test, PT-Milk and ultrasound-based sensor results.

The data sets were filtered for unreliable measurements. In this experiment, initially unreliable results were eliminated on the basis that they were visually inconsistent with the other results for that animal. PT-Milk fat and protein results that were visually inconsistent with the trend for that animal were marked as outliers. If either fat or protein were identified as outliers, both fat and protein results from PT-Milk were excluded from subsequent analyses. Ultrasound-based sensor fat and protein results were marked as outliers and excluded from subsequent analyses in the same way.

Performance statistics were only calculated on results from milkings with valid PT-Milk, ultrasound-based sensor and herd test results ("fully matched milkings") from the 31 cows with more than 8 fully matched milkings. Standard deviation and average of error was determined for individual test results from PT-Milk and ultrasound-based sensors, using the herd test results as a ground truth. Standard deviation and average of error of cow mean values was also determined as a measure of animal specific bias within the herd.

Figure 3:
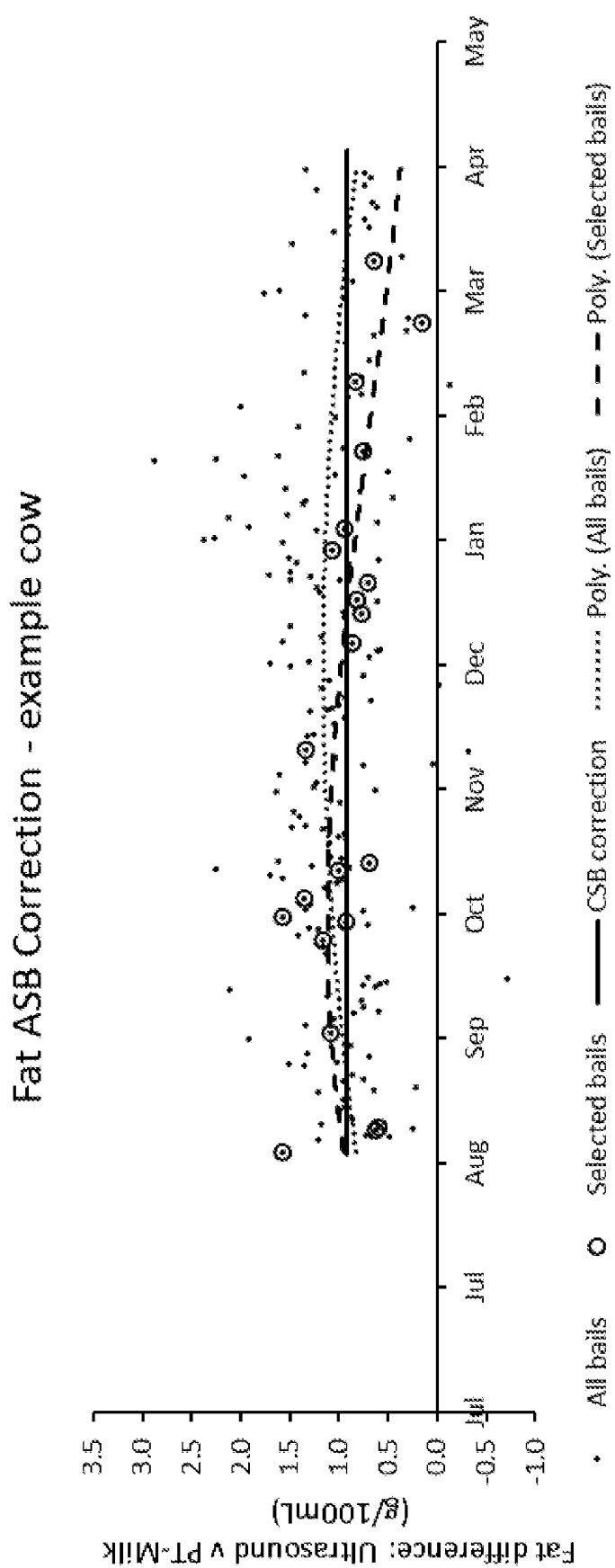
FIG. 3 is a scatterplot of milk fat error results from a first type sensor against a second type sensor for an individual animal.
Figure 4A:
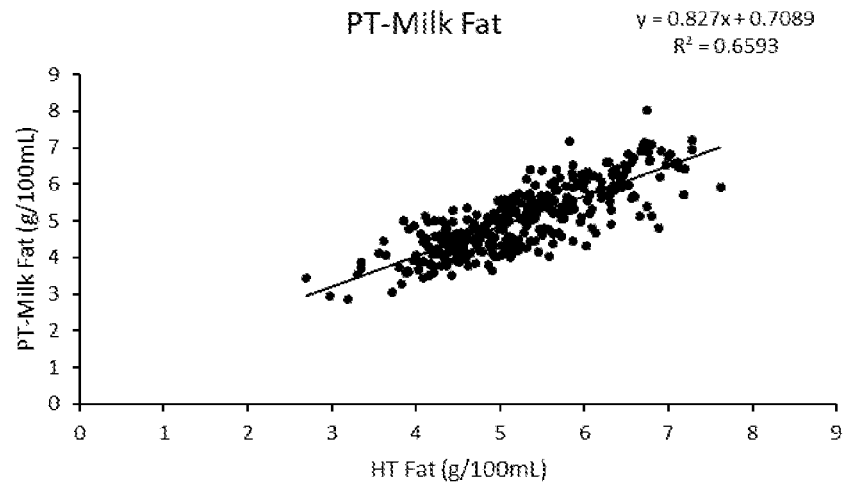
FIG. 4A-4C are scatterplots showing correlation between sensor results and herd test results for three measurement types (first type sensor, second type sensor, animal specific bias corrected first type sensor) for fat at an individual milking level.
Figure 4B:
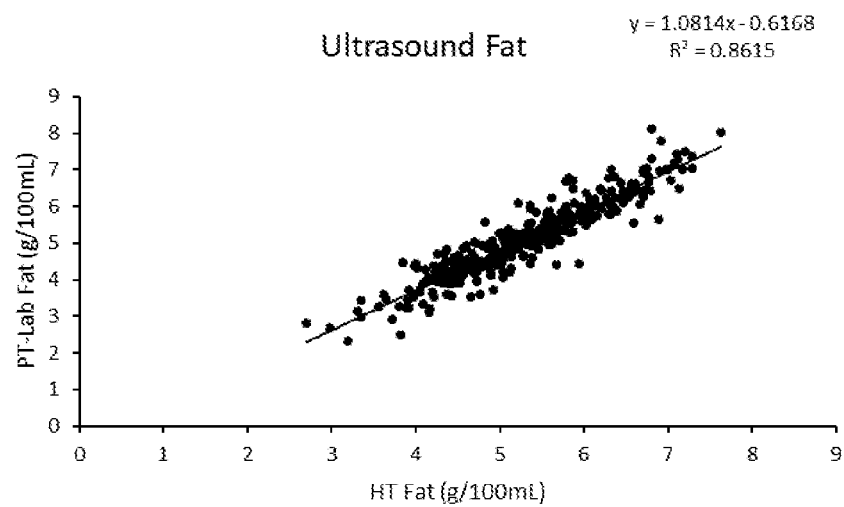
Figure 4C:
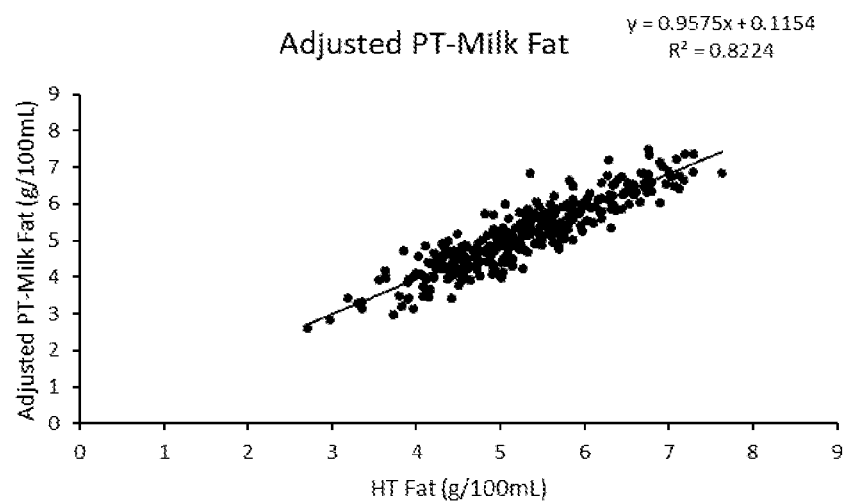
Figure 5A:
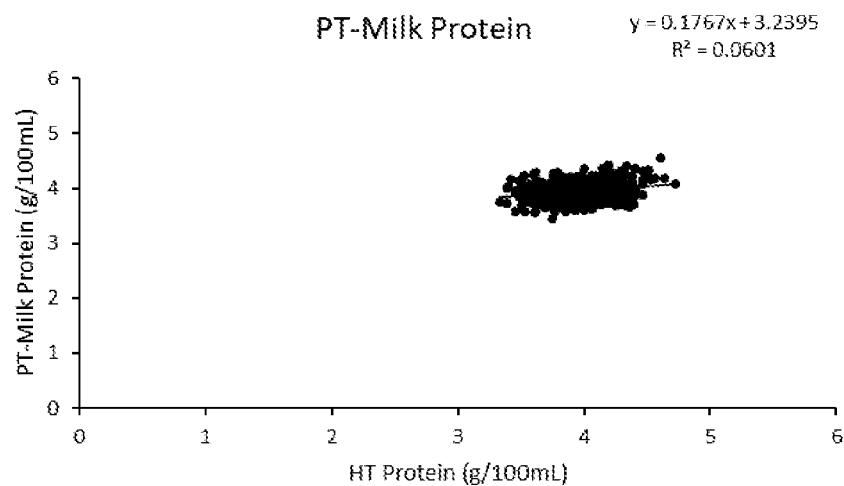
FIG. 5A-5C is a collection of scatterplots showing correlation between sensor results and herd test results for three measurement types (first type sensor, second type sensor, animal specific bias corrected first type sensor) for protein at an individual milking level.
Figure 5B:
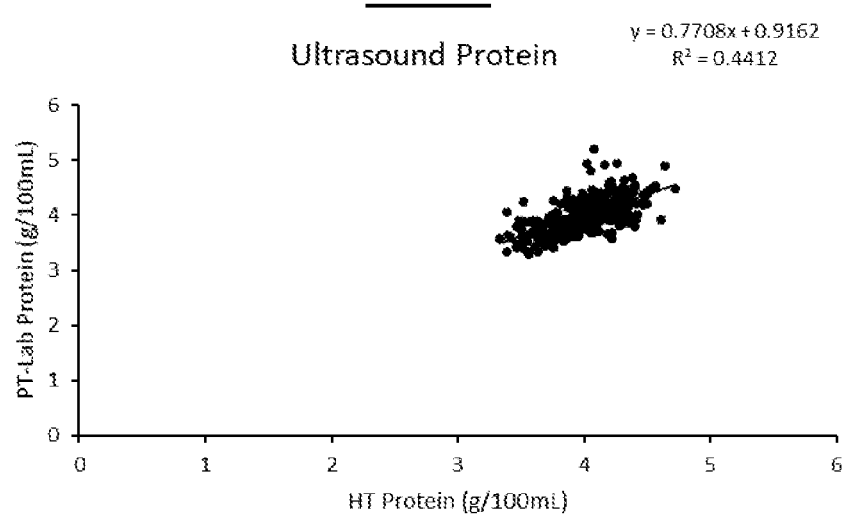
Figure 5C:
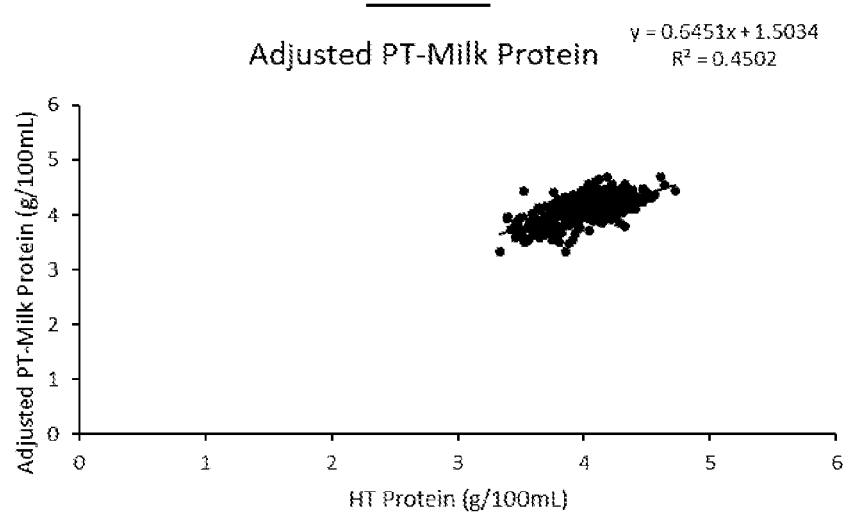
Figure 6A:
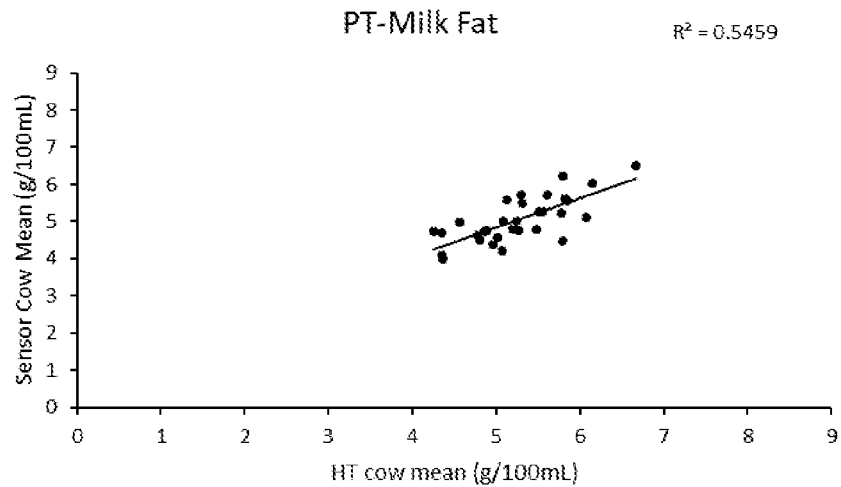
FIG. 6A-6C is a collection of scatterplots showing correlation between sensor results and herd test results for three measurement types (first type sensor, second type sensor, animal specific bias corrected first type sensor) for fat at a cow mean level.
Figure 6B:
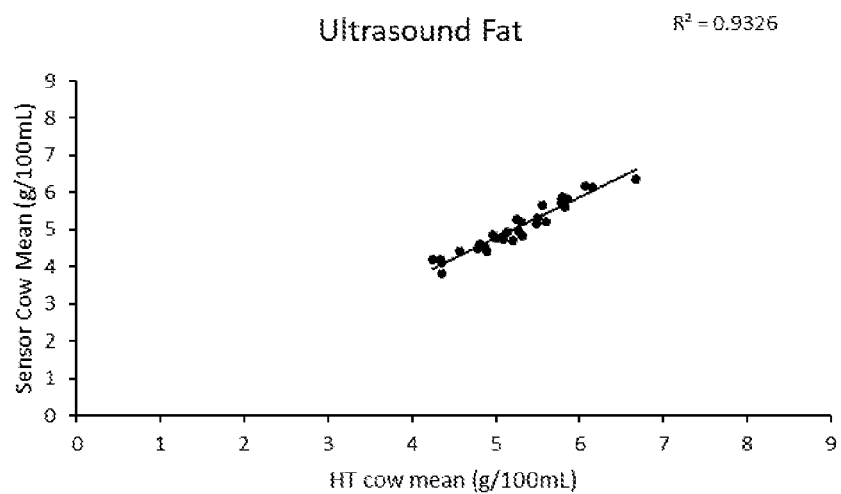
Figure 6C:
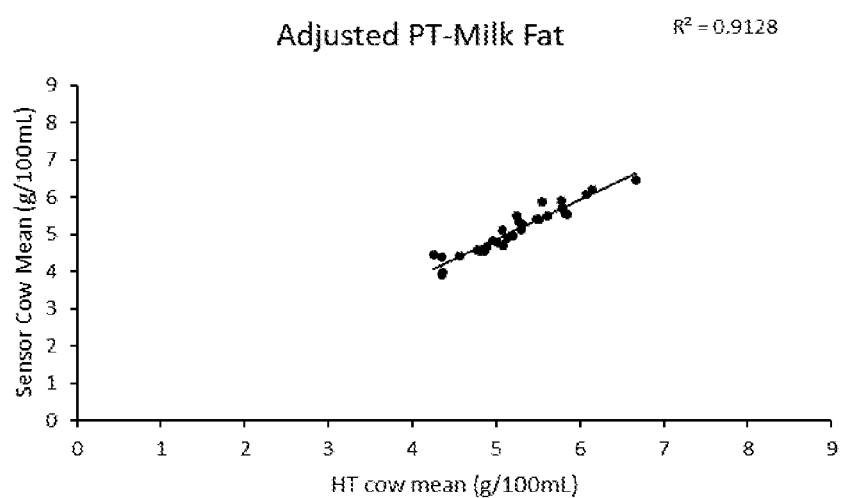
Figure 7A:
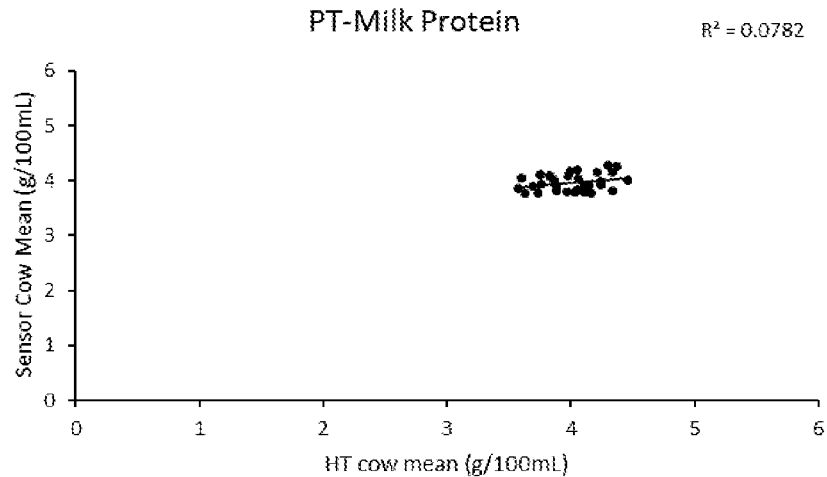
FIG. 7A-7C is a collection of scatterplots showing correlation between sensor results and herd test results for three measurement types (first type sensor, second type sensor, animal specific bias corrected first type sensor) for protein at a cow mean level.
Figure 7B:
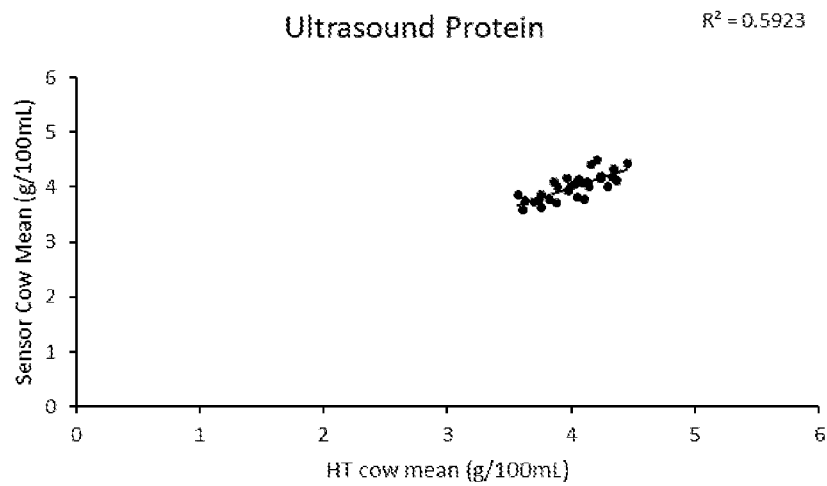
Figure 7C:
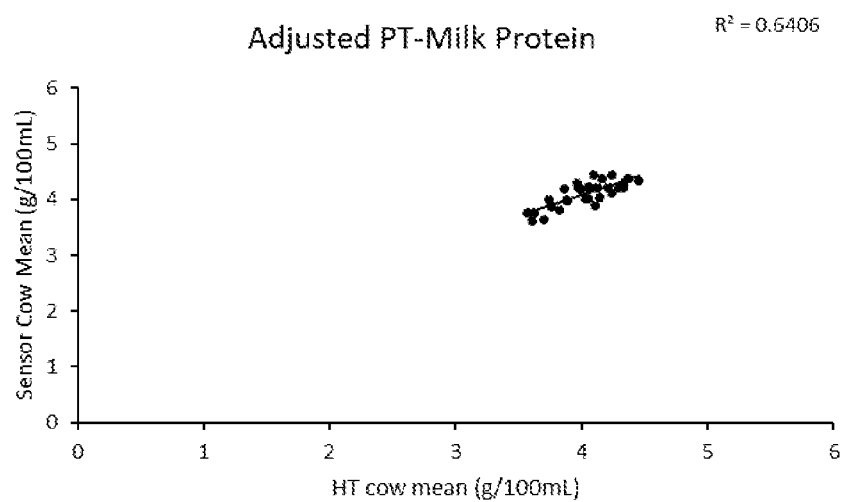

An animal specific bias (ASB) correction for each cow was determined using an assumption that 6% bail coverage (2/34 bails) would provide a sufficient number of tests to estimate animal specific bias. For two of the bails with system sensors (bails 2 and 3) all milkings with valid PT-Milk and ultrasound-based results were used to calculate an ASB correction for each of the 31 cows. This was a minimum of 13 milkings and an average of 21 milkings per cow. FIG. 3 shows the difference between ultrasound and PT-Milk results for an example cow, where the circles denote measurements on bails 2 or 3, which were used to calculate the ASB correction for this cow (denoted by the solid line). The fat ASB correction for each cow was calculated as the cow-mean difference between ultrasound-based and PT-Milk fat results. The protein ASB correction for each cow was calculated in the same way using the protein results. All PT-Milk results were adjusted using the individual ASB corrections. Performance statistics were calculated on the adjusted PT-Milk results, as noted above.

Table 1, FIGS. 4A-4C, FIGS. 5A-5C, FIGS. 6A-6C and FIGS. 7A-7C show the performance of the three milk composition estimates: PT-Milk, ultrasound-based second type sensor, and PT-Milk adjusted using the ASB corrections ("adjusted PT-Milk").

TABLE 1

Performance statistics (g/100 mL) for the three milk composition estimates at individual test and cow mean levels.

| | Fat | | | Protein | | |
| --- | --- | --- | --- | --- | --- | --- |
| | PT-Milk | Ultrasound-based system sensor | Adjusted PT-Milk | PT-Milk | Ultrasound-based system sensor | Adjusted PT-Milk |
| SD of error | 0.55 | 0.39 | 0.40 | 0.24 | 0.40 | 0.22 |
| Avg error | −0.20 | −0.19 | −0.11 | −0.05 | 0.00 | +0.08 |
| SD of cow mean error | 0.43 | 0.18 | 0.19 | 0.25 | 0.16 | 0.15 |
| Avg cow mean error | −0.20 | −0.20 | −0.11 | −0.05 | −0.01 | +0.08 |

At a cow mean level, the standard deviation (SD) of cow mean error values for PT-Milk and ultrasound-based sensors were consistent with those obtained previously in separate experiments. The SD of cow mean error values for adjusted PT-Milk were less than those for PT-Milk: the SD of cow mean error of adjusted PT-Milk for fat was 0.19 g/100 mL compared to 0.43 g/100 mL for PT-Milk alone, for protein the SD of cow mean error was 0.15 g/100 mL compared to 0.25 g/100 mL for PT-Milk alone. From this, it may be seen that the effect of ASB was reduced significantly through application of the respective ASB corrections.

Further, the adjusted PT-Milk SD of cow mean error was similar to that of the ultrasound-based sensing method. This shows that the low ASB of ultrasound-based second type sensing can be achieved on PT-Milk using a ASB correction determined from ultrasound-based sensors installed at just 6% of bails (2 out of a total of 34 in this instance). This allows for the use of the lower cost PT-Milk sensors to achieve a high bail coverage with a higher precision.

At an individual test level, the SD of error for PT-Milk was 0.55 and 0.24 g/100 mL for fat and protein respectively. This is consistent with the performance of this technology measured previously. The SD of error for ultrasound-based fat (0.39 g/100 mL) was similar to that previously measured, but the SD of error for ultrasound-based protein (0.40 g/100 mL) was somewhat higher than measured previously. The inventor has hypothesised that this may be due to a relatively weak outlier detection method applied in this experiment, and that if more rigorous outlier detection were applied the ultrasound-based protein SD of error may be expected to improve.

The inventor observed that the SD of error for adjusted PT-Milk protein (0.22 g/100 mL) was superior to ultrasound-based protein (0.40 g/100 mL). It is believed that the reason for this may be that a large proportion of the ultrasound-based error is random error. The ASB correction is averaged across many tests comparing PT-Milk and ultrasound-based results, which is believed to reduce random error resulting in a good estimate of ASB. By contrast, PT-Milk error is believed to be mostly ASB, so when the ASB correction is applied to individual results, a very good individual measure is obtained.

The inventor notes that the implementation in this experiment was relatively simple. More sophisticated approaches could be used, perhaps improving the resulting ASB correction. For example, the outlier detection of ultrasound-based measurements is considered to be an area for refinement, and the exclusion of outliers on the basis that they are out of trend for the cow may be automated. Another layer of individual cow outlier detection could also be applied on the individual ASB estimates.

Further, in this experiment the ASB correction was constant across the period during which data was corrected. For completeness, it is envisaged that the ASB correction may be adjusted throughout the lactation—for example using the polynomial curve fitted to the selected bails, as shown in FIG. 3.

The present technology provides methods and systems for correcting animal specific bias in automated milk analysis sensors susceptible to such bias.

The entire disclosures of all applications, patents and publications cited above are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

Aspects of the present invention have been described by way of example only and it should be appreciated that modifications and additions may be made thereto without departing from the scope thereof.

The invention claimed is:

1. A system for analysing milk, including:
a plurality of first type sensors, each first type sensor associated with a respective one of a plurality of milking clusters of a milking system and configured to analyse milk extracted from an individual animal by the milking cluster to determine at least one first type sensor value of a parameter of the milk across an event period;
at least one of a second type sensor associated with at least one of the plurality of milking clusters and configured to analyse the milk extracted from the individual animal by the milking cluster to determine at least one second type sensor value of the parameter of the milk within the event period, wherein the second type sensor is less susceptible to animal specific bias than the first type sensor, and wherein the number of the second type sensor in the system is less than the number of first type sensors; and
at least one processor configured to:
determine an animal specific bias correction for the individual animal based on the at least one first type sensor value of the parameter and the at least one second type sensor value of the parameter determined for the individual animal; and
applying the animal specific bias correction to first type sensor values of the parameter obtained from the first type sensors for milk extracted from the individual animal.

2. The system of claim 1, wherein the first type sensors are optical sensors.

3. The system of claim 1, wherein the first type sensors are in-line sensors.

4. The system of claim 1, wherein the at least one second type sensor utilises measurement techniques including one or more of: ultrasound, acoustics, electromagnetic radiation, and electronic impedance.

5. The system of claim 1, wherein determining of the animal specific bias value by the at least one processor includes determining a difference between the first type sensor value of the parameter and the second type sensor value of the parameter each time the animal is milked using a milking cluster having an associated first type sensor and second type sensor.

6. The system of claim 5, wherein determining of the animal specific bias value by the at least one processor includes determining an average of the difference between the first type sensor value of the parameter and the second type sensor value of the parameter over a time period including a plurality of instances of the animal being milked.

7. The system of claim 6, wherein the time period is a full lactation.

8. The system of claim 6, wherein the time period is part of a lactation.

9. The system of claim 6, wherein the animal specific bias correction is a moving animal specific bias correction used from the start of the time period.

10. The system of claim 1, wherein determining of the animal specific bias value by the at least one processor includes determining the animal specific bias correction accounting for trends across a time period.

11. The system of claim 10, wherein the animal specific bias value is determined by fitting a curve to a relationship of the difference between the first type sensor value of the parameter and the second type sensor value of the parameter over the time period.

12. The system of claim 1, wherein the at least one processor is configured to apply the animal specific bias correction retrospectively.

13. The system of claim 1, wherein determining of the animal specific bias correction by the at least one processor includes excluding data from an instance of the animal being milked where the first type sensor value of the parameter and/or the second type sensor value of the instance are determined to be outliers.

14. The system of claim 1, wherein the parameter of the milk is fat.

15. The system of claim 1, wherein the parameter of the milk is protein.

16. The system of claim 1, wherein each of the first type sensors and the at least one second type sensor is configured to determine values for a plurality of parameters of the milk, wherein the plurality of parameters include at least milk and fat.

17. A method for analysing milk in a system having a plurality of milking clusters, each configured to extract milk from an individual animal, the method including:
analysing milk extracted from an individual animal by a milking cluster, using a first type sensor associated with the milking cluster, to determine at least one first type sensor value of a parameter of the milk across an event period;
analysing the milk extracted from the individual animal by the milking cluster, using a second type sensor associated with the milking cluster, to determine at least one second type sensor value of the parameter of the milk within the event period, wherein the second type sensor is less susceptible to animal specific bias than the first type sensor, and wherein the number of the second type sensor in the system is less than the number of first type sensors; and
determining an animal specific bias correction for the individual animal based on the at least one first type sensor value of the parameter and the at least one second type sensor value of the parameter determined for the individual animal; and
applying the animal specific bias correction to the first type sensor values of the parameter obtained from the first type sensors for milk extracted from the individual animal.

* * * * *